United States Patent
Cumming (10) Patent No.: US 9,034,036 B2
(45) Date of Patent: *May 19, 2015

(54) SEAMLESS-VISION, TILTED INTRAOCULAR LENS

(71) Applicant: James Stuart Cumming, Laguna Beach, CA (US)

(72) Inventor: James Stuart Cumming, Laguna Beach, CA (US)

(73) Assignee: James Stuart Cumming, Laguna Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/953,605

(22) Filed: Jul. 29, 2013

(65) Prior Publication Data

US 2014/0172093 A1     Jun. 19, 2014

Related U.S. Application Data

(63) Continuation of application No. 13/472,354, filed on May 15, 2012, now Pat. No. 8,523,942, and a continuation of application No. 13/111,599, filed on May 19, 2011, and a continuation of application No. 13/092,359, filed on Apr. 22, 2011.

(51) Int. Cl.
    *A61F 2/16*     (2006.01)

(52) U.S. Cl.
    CPC ............ *A61F 2/1613* (2013.01); *A61F 2/1616* (2013.01); *A61F 2002/1689* (2013.01); *A61F 2/1627* (2013.01)

(58) Field of Classification Search
    CPC ... A61F 2/1616; A61F 2/1624; A61F 2/1627; A61F 2002/1681; A61F 2002/1689

USPC ............ 623/6.37, 6.43, 6.46, 6.38, 6.4, 6.44, 623/6.45, 6.47, 6.49
    See application file for complete search history.

(56) References Cited

U.S. PATENT DOCUMENTS

| | | | |
|---|---|---|---|
| 2,834,023 | A | 5/1958 | Lieb |
| 4,073,014 | A | 2/1978 | Poler |
| 4,118,808 | A | 10/1978 | Poler |
| 4,122,556 | A | 10/1978 | Poler |
| 4,159,546 | A | 7/1979 | Shearing |
| 4,168,547 | A | 9/1979 | Konstantinov et al. |
| 4,173,798 | A | 11/1979 | Welsh |
| 4,174,543 | A | 11/1979 | Kelman |
| 4,206,518 | A | 6/1980 | Jardon et al. |
| 4,244,060 | A | 1/1981 | Hoffer |

(Continued)

FOREIGN PATENT DOCUMENTS

| | | |
|---|---|---|
| CA | 2110184 A1 | 12/1992 |
| CH | 681687 | 5/1993 |

(Continued)

OTHER PUBLICATIONS

Dykstra, M., et al. Biological Electron Microscopy: Theory, Techniques, and Troublshooting, 2003, p. 81.

(Continued)

*Primary Examiner* — David H Willse
*Assistant Examiner* — Javier Blanco
(74) *Attorney, Agent, or Firm* — Knobbe Martens Olson & Bear LLP (57) ABSTRACT

A variable focus intraocular lens comprises an optic coupled to at least one haptic at a rigid flexion that sets a non-zero angle between the optic and the haptic.

7 Claims, 9 Drawing Sheets

(56) References Cited

U.S. PATENT DOCUMENTS

| | | |
|---|---|---|
| 4,254,509 A | 3/1981 | Tennant |
| 4,277,851 A | 7/1981 | Choyce et al. |
| 4,298,995 A | 11/1981 | Poler |
| 4,304,012 A | 12/1981 | Richard |
| 4,409,690 A | 10/1983 | Gess |
| 4,409,691 A | 10/1983 | Levy |
| 4,424,597 A | 1/1984 | Schlegel |
| 4,441,217 A | 4/1984 | Cozean, Jr. |
| 4,477,931 A | 10/1984 | Kelman |
| 4,573,998 A | 3/1986 | Mazzocco |
| 4,585,457 A | 4/1986 | Kalb |
| 4,605,411 A | 8/1986 | Fedorov et al. |
| 4,629,462 A | 12/1986 | Feaster |
| 4,648,878 A * | 3/1987 | Kelman ............... 623/6.26 |
| 4,664,665 A | 5/1987 | Reuss et al. |
| 4,664,666 A | 5/1987 | Barrett |
| 4,673,406 A | 6/1987 | Schlegel |
| 4,676,790 A | 6/1987 | Kern |
| 4,681,102 A | 7/1987 | Bartell |
| 4,704,123 A | 11/1987 | Smith |
| 4,710,195 A | 12/1987 | Giovinazzo |
| 4,718,904 A | 1/1988 | Thornton |
| 4,737,322 A | 4/1988 | Bruns et al. |
| 4,738,680 A | 4/1988 | Herman |
| 4,743,254 A | 5/1988 | Davenport |
| 4,753,655 A | 6/1988 | Hecht |
| 4,759,761 A | 7/1988 | Portnoy |
| 4,763,650 A | 8/1988 | Hauser |
| 4,765,329 A | 8/1988 | Cumming et al. |
| 4,769,033 A | 9/1988 | Nordan |
| 4,769,035 A | 9/1988 | Kelman |
| 4,778,463 A | 10/1988 | Hetland |
| 4,781,719 A | 11/1988 | Kelman |
| 4,790,847 A | 12/1988 | Woods |
| 4,793,344 A | 12/1988 | Cumming et al. |
| 4,813,955 A | 3/1989 | Achatz et al. |
| 4,816,030 A | 3/1989 | Robinson |
| 4,840,627 A | 6/1989 | Blumenthal |
| 4,842,601 A | 6/1989 | Smith |
| 4,846,833 A | 7/1989 | Cumming |
| 4,862,885 A | 9/1989 | Cumming |
| 4,868,251 A | 9/1989 | Reich et al. |
| 4,880,427 A | 11/1989 | Anis |
| 4,888,012 A | 12/1989 | Horn et al. |
| 4,892,543 A | 1/1990 | Turley |
| 4,919,130 A | 4/1990 | Stoy et al. |
| 4,932,966 A | 6/1990 | Christie et al. |
| 4,932,968 A | 6/1990 | Caldwell et al. |
| 4,932,970 A | 6/1990 | Portney |
| 4,936,850 A | 6/1990 | Barrett |
| 4,963,148 A | 10/1990 | Sulc et al. |
| 4,969,897 A | 11/1990 | Kalb |
| 4,976,716 A | 12/1990 | Cumming |
| 4,978,354 A | 12/1990 | Van Gent |
| 4,994,082 A | 2/1991 | Richards et al. |
| 5,047,051 A | 9/1991 | Cumming |
| 5,066,297 A | 11/1991 | Cumming |
| 5,078,742 A | 1/1992 | Dahan |
| 5,141,507 A | 8/1992 | Parekh |
| 5,152,788 A | 10/1992 | Isaacson et al. |
| 5,152,789 A | 10/1992 | Willis |
| 5,171,319 A | 12/1992 | Keates et al. |
| 5,171,320 A | 12/1992 | Nishi |
| 5,180,390 A | 1/1993 | Drews |
| 5,217,490 A | 6/1993 | Sayano et al. |
| 5,275,604 A | 1/1994 | Rheinish et al. |
| 5,275,623 A | 1/1994 | Sarfarazi |
| 5,275,624 A | 1/1994 | Hara et al. |
| 5,290,310 A | 3/1994 | Makower et al. |
| 5,304,182 A | 4/1994 | Rheinish et al. |
| 5,324,306 A | 6/1994 | Makower et al. |
| 5,326,347 A | 7/1994 | Cumming |
| 5,366,502 A | 11/1994 | Patel |
| 5,376,115 A | 12/1994 | Jansen |
| 5,425,734 A | 6/1995 | Blake |
| 5,443,506 A | 8/1995 | Garabet |
| 5,474,562 A | 12/1995 | Orchowski et al. |
| 5,476,514 A | 12/1995 | Cumming |
| 5,489,302 A | 2/1996 | Skottun |
| 5,496,366 A | 3/1996 | Cumming |
| 5,522,891 A | 6/1996 | Klaas |
| 5,562,731 A | 10/1996 | Cumming |
| 5,578,042 A | 11/1996 | Cumming |
| 5,578,078 A | 11/1996 | Nakajima et al. |
| 5,607,472 A | 3/1997 | Thompson |
| 5,611,968 A | 3/1997 | Grisoni et al. |
| 5,674,282 A | 10/1997 | Cumming |
| 5,686,414 A | 11/1997 | Scannon |
| 5,699,142 A | 12/1997 | Lee et al. |
| 5,716,403 A | 2/1998 | Tran et al. |
| 5,800,532 A | 9/1998 | Lieberman |
| 5,837,156 A | 11/1998 | Cumming |
| 5,843,187 A | 12/1998 | Bayers |
| 5,873,879 A | 2/1999 | Figueroa et al. |
| 5,919,230 A | 7/1999 | Sambursky |
| 5,944,725 A | 8/1999 | Cicenas et al. |
| 5,968,094 A | 10/1999 | Werblin et al. |
| 5,984,914 A | 11/1999 | Cumming |
| 6,007,579 A | 12/1999 | Lipshitz et al. |
| 6,013,101 A | 1/2000 | Israel |
| 6,015,435 A | 1/2000 | Valunin et al. |
| 6,027,531 A | 2/2000 | Tassignon |
| 6,051,024 A | 4/2000 | Cumming |
| 6,066,171 A | 5/2000 | Lipshitz et al. |
| 6,066,172 A | 5/2000 | Huo et al. |
| 6,113,633 A | 9/2000 | Portney |
| 6,129,760 A | 10/2000 | Fedorov et al. |
| 6,161,544 A | 12/2000 | DeVore |
| 6,164,282 A | 12/2000 | Gwon et al. |
| 6,176,878 B1 | 1/2001 | Gwon et al. |
| 6,179,870 B1 | 1/2001 | Sourdille et al. |
| 6,193,750 B1 | 2/2001 | Cumming |
| 6,197,058 B1 | 3/2001 | Portney |
| 6,197,059 B1 | 3/2001 | Cumming |
| 6,217,612 B1 | 4/2001 | Woods |
| 6,299,641 B1 | 10/2001 | Woods |
| 6,302,911 B1 | 10/2001 | Hanna |
| 6,322,589 B1 | 11/2001 | Cumming |
| 6,342,073 B1 | 1/2002 | Cumming et al. |
| 6,387,126 B1 | 5/2002 | Cumming |
| 6,391,056 B2 | 5/2002 | Cumming |
| 6,406,494 B1 | 6/2002 | Laguette et al. |
| 6,409,763 B1 | 6/2002 | Brady |
| 6,413,276 B1 | 7/2002 | Werblin |
| 6,419,697 B1 | 7/2002 | Kelman |
| 6,423,094 B1 | 7/2002 | Sarfarazi |
| 6,443,985 B1 | 9/2002 | Woods |
| 6,451,056 B1 | 9/2002 | Cumming |
| 6,461,384 B1 | 10/2002 | Hoffmann et al. |
| 6,488,708 B2 | 12/2002 | Sarfarazi |
| 6,494,911 B2 | 12/2002 | Cumming |
| 6,497,708 B1 | 12/2002 | Cumming |
| 6,503,275 B1 | 1/2003 | Cumming |
| 6,503,276 B2 | 1/2003 | Lang et al. |
| 6,517,577 B1 | 2/2003 | Callahan et al. |
| 6,524,340 B2 | 2/2003 | Israel |
| 6,540,353 B1 | 4/2003 | Dunn |
| 6,558,420 B2 | 5/2003 | Green |
| 6,613,343 B2 | 9/2003 | Dillingham et al. |
| 6,616,691 B1 | 9/2003 | Tran |
| 6,616,692 B1 | 9/2003 | Glick et al. |
| 6,638,305 B2 | 10/2003 | Laguette |
| 6,638,306 B2 | 10/2003 | Cumming |
| 6,645,245 B1 | 11/2003 | Preussner |
| 6,660,035 B1 | 12/2003 | Lang et al. |
| 6,660,036 B2 | 12/2003 | Cumming |
| 6,685,741 B2 | 2/2004 | Landreville et al. |
| 6,695,881 B2 | 2/2004 | Peng et al. |
| 6,749,634 B2 | 6/2004 | Hanna |
| 6,767,363 B1 | 7/2004 | Bandhauer et al. |
| 6,849,091 B1 | 2/2005 | Cumming |
| 6,858,040 B2 | 2/2005 | Nguyen et al. |
| 6,881,225 B2 | 4/2005 | Okada |
| 6,884,263 B2 | 4/2005 | Valyunin |

(56) References Cited

U.S. PATENT DOCUMENTS

| | | |
|---|---|---|
| 6,921,416 B2 | 7/2005 | Khoury |
| 6,926,736 B2 | 8/2005 | Peng |
| 6,969,403 B2 | 11/2005 | Peng |
| 6,972,033 B2 | 12/2005 | McNicholas |
| 7,018,409 B2 | 3/2006 | Glick |
| 7,025,783 B2 | 4/2006 | Brady |
| 7,037,338 B2 | 5/2006 | Nagamoto |
| 7,048,760 B2 | 5/2006 | Cumming |
| 7,097,660 B2 | 8/2006 | Portney |
| 7,125,422 B2 | 10/2006 | Woods et al. |
| 7,150,759 B2 | 12/2006 | Paul et al. |
| 7,150,760 B2 | 12/2006 | Zhang |
| 7,229,475 B2 | 6/2007 | Glazier |
| 7,229,476 B2 | 6/2007 | Azar |
| 7,300,464 B2 | 11/2007 | Tran |
| 7,326,246 B2 | 2/2008 | Brady |
| 7,341,599 B1 | 3/2008 | Peyman |
| 7,435,258 B2 | 10/2008 | Blake |
| 7,435,259 B2 | 10/2008 | Cumming |
| 7,553,327 B2 | 6/2009 | Cumming |
| 7,662,180 B2 | 2/2010 | Paul et al. |
| 7,763,070 B2 | 7/2010 | Cumming |
| 7,837,730 B2 | 11/2010 | Cumming |
| 7,981,155 B2 | 7/2011 | Cumming |
| 7,985,253 B2 | 7/2011 | Cumming |
| 8,038,711 B2 | 10/2011 | Clarke |
| 8,080,056 B2 | 12/2011 | Cumming |
| 8,100,965 B2 | 1/2012 | Cumming et al. |
| 8,109,998 B2 | 2/2012 | Cumming |
| 8,163,015 B2 | 4/2012 | Cumming |
| 8,216,308 B2 | 7/2012 | Blake et al. |
| 8,523,942 B2 | 9/2013 | Cumming |
| 8,734,512 B2 | 5/2014 | Cumming |
| 8,764,823 B2 | 7/2014 | Cumming |
| 2001/0001836 A1 | 5/2001 | Cumming |
| 2002/0120329 A1 | 8/2002 | Lang et al. |
| 2003/0060881 A1 | 3/2003 | Glick et al. |
| 2003/0078658 A1 | 4/2003 | Zadno-Azizi |
| 2003/0097177 A1 | 5/2003 | Tran |
| 2003/0109925 A1 | 6/2003 | Ghazizadeh et al. |
| 2003/0135272 A1 | 7/2003 | Brady et al. |
| 2003/0142269 A1 | 7/2003 | Cumming |
| 2003/0171808 A1 | 9/2003 | Phillips |
| 2003/0171809 A1 | 9/2003 | Phillips |
| 2003/0187505 A1 | 10/2003 | Liao |
| 2003/0199977 A1 | 10/2003 | Cumming |
| 2003/0204257 A1 | 10/2003 | Southard |
| 2004/0002757 A1 | 1/2004 | Lai et al. |
| 2004/0015236 A1 | 1/2004 | Sarfarazi |
| 2004/0082993 A1 | 4/2004 | Woods |
| 2004/0111152 A1 | 6/2004 | Kelman |
| 2004/0148023 A1 | 7/2004 | Shu |
| 2004/0215207 A1 | 10/2004 | Cumming |
| 2004/0220666 A1 | 11/2004 | Cumming |
| 2004/0249456 A1 | 12/2004 | Cumming |
| 2005/0021140 A1 | 1/2005 | Liao |
| 2005/0027354 A1 | 2/2005 | Brady et al. |
| 2005/0096741 A1 | 5/2005 | Cumming |
| 2005/0107875 A1 | 5/2005 | Cumming |
| 2005/0125058 A1 | 6/2005 | Cumming et al. |
| 2005/0137703 A1 | 6/2005 | Chen |
| 2005/0267576 A1 | 12/2005 | Cumming |
| 2005/0288784 A1 | 12/2005 | Peyman |
| 2006/0064077 A1 | 3/2006 | Peyman |
| 2006/0064162 A1 | 3/2006 | Klima |
| 2006/0100704 A1 | 5/2006 | Blake et al. |
| 2006/0111776 A1 | 5/2006 | Glick et al. |
| 2006/0116764 A1 | 6/2006 | Simpson |
| 2006/0149369 A1 | 7/2006 | Cumming et al. |
| 2007/0032867 A1 | 2/2007 | Cumming |
| 2007/0129800 A1 | 6/2007 | Cumming |
| 2007/0129803 A1 | 6/2007 | Cumming et al. |
| 2007/0135915 A1 | 6/2007 | Klima |
| 2007/0142908 A1 | 6/2007 | Xu |
| 2007/0198084 A1 | 8/2007 | Cumming et al. |
| 2008/0027538 A1 | 1/2008 | Cumming |
| 2008/0027539 A1 * | 1/2008 | Cumming ............ 623/6.37 |
| 2008/0027540 A1 | 1/2008 | Cumming |
| 2008/0046077 A1 | 2/2008 | Cumming |
| 2008/0086208 A1 | 4/2008 | Nordan |
| 2008/0154362 A1 | 6/2008 | Cumming |
| 2008/0281415 A1 | 11/2008 | Cumming |
| 2008/0281416 A1 | 11/2008 | Cumming |
| 2008/0288066 A1 | 11/2008 | Cumming |
| 2008/0294254 A1 | 11/2008 | Cumming et al. |
| 2008/0319545 A1 | 12/2008 | Cumming |
| 2009/0005866 A1 | 1/2009 | Cumming |
| 2009/0234449 A1 | 9/2009 | De Juan, Jr. et al. |
| 2010/0004742 A1 | 1/2010 | Cumming |
| 2010/0057202 A1 | 3/2010 | Bogaert |
| 2011/0313519 A1 | 12/2011 | Cumming |
| 2011/0313524 A1 | 12/2011 | Cumming |
| 2011/0313525 A1 | 12/2011 | Cumming |
| 2011/0313526 A1 | 12/2011 | Cumming |
| 2012/0310344 A1 | 12/2012 | Cumming |
| 2013/0073039 A1 | 3/2013 | Mirlay |
| 2014/0088699 A1 | 3/2014 | Cumming |
| 2014/0094909 A1 | 4/2014 | Cumming |
| 2014/0155871 A1 | 6/2014 | Cumming |

FOREIGN PATENT DOCUMENTS

| | | |
|---|---|---|
| DE | 3626869 | 2/1988 |
| FR | 2728458 | 6/1996 |
| FR | 2728459 | 6/1996 |
| FR | 2734472 | 11/1996 |
| FR | 2765797 | 1/1999 |
| FR | 2991572 A1 * | 12/2013 |
| GB | 2171912 | 9/1986 |
| GB | 2226246 | 6/1990 |
| JP | 2003-190193 | 7/2003 |
| SU | 1123685 A * | 11/1984 |
| WO | WO 93/05733 | 4/1993 |
| WO | WO 01/19288 | 3/2001 |
| WO | WO 01/19289 | 3/2001 |
| WO | WO 03017873 A1 * | 3/2003 |
| WO | WO 2007/037180 | 4/2007 |

OTHER PUBLICATIONS

Final Office Action for U.S. Appl. No. 13/017,189 dated Jul. 18, 2014 in 10 pages.

Final Office Action for U.S. Appl. No. 13/092,359 dated Mar. 5, 2013 in 11 pages.

Final Office Action for U.S. Appl. No. 13/111,599 dated May 2, 2013 in 10 pages.

Final Office Action for U.S. Appl. No. 13/155,327 dated Dec. 10, 2012 in 10 pages.

International Search Report and Written Opinion for PCT/US13/61452 dated Feb. 24, 2014 in 11 pages.

Office Action for U.S. Appl. No. 13/017,189 dated May 9, 2013 in 9 pages.

Office Action for U.S. Appl. No. 13/092,359 dated Oct. 25, 2012 in 10 pages.

Office Action for U.S. Appl. No. 13/092,359 dated Sep. 8, 2014 in 15 pages.

Office Action for U.S. Appl. No. 13/111,599 dated Jan. 2, 2013 in 11 pages.

Office Action for U.S. Appl. No. 13/111,599 dated Sep. 5, 2014 in 13 pages.

Office Action for U.S. Appl. No. 13/155,327 dated Jul. 20, 2012 in 7 pages.

Office Action for U.S. Appl. No. 13/155,327 dated Apr. 26, 2013 in 7 pages.

Office Action for U.S. Appl. No. 13/891,088 dated Aug. 13, 2014 in 25 pages.

Office Action for U.S. Appl. No. 13/910,076 dated Nov. 7, 2014 in 12 pages.

Office Action for U.S. Appl. No. 14/143,162 dated Aug. 4, 2014 in 18 pages.

(56) References Cited

OTHER PUBLICATIONS

Office Action for U.S. Appl. No. 14/257,933 dated Oct. 31, 2014 in 9 pages.
Response to Office Action for U.S. Appl. No. 13/017,189 dated Aug. 8, 2013 in 5 pages.
Response to Office Action for U.S. Appl. No. 13/092,359 dated Jan. 31, 2013 in 8 pages.
Response to Final Office Action for U.S. Appl. No. 13/092,359 dated Jul. 29, 2013 in 7 pages.
Response to Office Action for U.S. Appl. No. 13/111,599 dated Apr. 9, 2013 in 6 pages.
Response to Office Action for U.S. Appl. No. 13/111,599 dated Jul. 30, 2013 in 6 pages.
Response to Office Action for U.S. Appl. No. 13/155,327 dated Oct. 26, 2012 in 5 pages.
Response to Office Action for U.S. Appl. No. 13/155,327 dated Apr. 10, 2013 in 5 pages.
Response to Office Action for U.S. Appl. No. 13/155,327 dated Jul. 25, 2013 in 5 pages.
Response to Office Action for U.S. Appl. No. 13/891,088 dated Dec. 15, 2014 in 8 pages.

* cited by examiner

SEAMLESS-VISION, TILTED INTRAOCULAR LENS

CROSS-REFERENCE TO RELATED APPLICATIONS

This application is a continuation of U.S. patent application Ser. No. 13/472,354, filed May 15, 2012, now U.S. Pat. No. 8,523,942, U.S. patent application Ser. No. 13/111,599, filed May 19, 2011, and U.S. patent Ser. No. 13/092,359, filed Apr. 22, 2011, the contents and disclosures of which are fully incorporated herein by reference.

BACKGROUND OF THE INVENTION

Premium intraocular lenses commonly implanted during cataract surgery are categorized in three ways: accommodating, multifocal and toric intraocular lenses The best visual acuity is achieved with the single focus accommodating lenses. The optic of these lenses moves forward and backward upon constriction and relaxation of the ciliary muscle. However, for reading in dim lighting conditions, or for small print, weak reading glasses are often necessary.

Multifocal lenses focus light on the retina at either two or three focal lengths. Thus, there is more than one image on the retina simultaneously forcing patients to select the image they wish to perceive, which poses a problem for patients unable to adjust their focal point. This creates additional problems in that the amount of light in focus is divided between the multiple focal points, and contrast sensitivity is thereby reduced, making vision at all distances difficult in dim lighting. In addition, there are severe problems when driving at night when the pupil is dilated. Many patients experience severe glare and halos and many have had to have the multifocal lenses explanted and replaced with a single vision standard lens, because of this problem. However, the near vision with the multifocal lenses is superior to that of the current accommodating lens.

Toric lenses correct eyes that have significant astigmatism.

The currently marketed plate accommodating intraocular lenses provide excellent distance and intermediate vision but sometimes require weak, +1.00, reading glasses for prolonged reading, for seeing small print, or reading in dim lighting conditions.

It is desirable to provide a single vision intraocular lens that will allow seamless vision at all distances. However, without excellent uncorrected distance vision there is no point in implanting lenses designed to give seamless vision from far to near.

Furthermore, it is important for intraocular lenses to have a consistent location along the axis of the eye to provide good uncorrected distance vision and to center in the middle of the vertical meridian of the eye.

The original intraocular lens consisted of a single optic. These lenses frequently de-centered and dislocated and it was discovered that there was a need to center and fixate the lens optic in the vertical meridian of the eye.

Attachments to the optic that center and fixate the lens within the capsular bag are called haptics. Traditionally, haptics consist of multiple flexible loops of various designs, J loops, C loops, closed loops and flexible radial arms. Recently, traditional haptics have been replaced in some lens designs with oblong, flat flexible plates, called plate haptics. These plate haptics usually made from silicone, are solid, flat, flexible and between 3.0 and 6.0 mm in width, 0.20 to 0.75 mm thick, and may have tapered, rounded or parallel sides. Plate haptics often have flexible loops or fingers that help center and fixate the lens within the capsular bag. These flexible fingers extend beyond the distal or outer end of the plate haptics and slightly beyond the diameter of the capsular bag and are designed to flex centrally to center and fixate the lens and its optic within the capsular bag.

An intraocular lens (IOL) is a lens implanted into the eye, usually replacing a normal human lens that has been clouded over by a cataract, or can replace a normal human lens as a form of refractive surgery to change the eye's optical power.

An accommodating IOL (AIOL) permits refocusing by means of movement along the optical axis in response to the constriction or relaxation of ciliary muscles. Near vision results from a forward movement of the optic on constriction of the ciliary muscle, which causes an increase in the pressure in the posterior part of the eye with a simultaneous decrease in pressure in the anterior part of the eye. Distance vision results from the reverse pressure change that takes place upon relaxation of the ciliary muscle and the resultant backwards movement of the lens. The movement of the optic enables the patient implanted with the lens to automatically change their vision between far, intermediate and near.

IDLs are known to consist of opposing haptics positioned on either side of a lens optic. Once a patient's cataract is removed, by e.g. phacoemulsification, the IOL is folded and placed into the capsular bag via what is typically a 3-4 mm incision. The haptics help to center the IOL and fixate it within the capsular bag by fibrosis. Such AIOLs are described in U.S. Pat. No. 5,674,282, U.S. Pat. No. 5,476,514, and U.S. Pat. No. 5,496,366, to Cumming, herein incorporated by reference in its entirety.

However, due to its construction, the lens optic of a traditional plate haptic lens is limited in its response to the change in vitreous pressure. Furthermore, when a plate haptic lens is placed within the capsular bag of the eye the peripheral circumferential remains of the anterior capsule and the posterior capsule of the human capsular bag, fibrose over the distal ends of the plates. The area of fibrosis can vary and sometimes covers only the distal 1.0 mm of the tip of the plate. With inadequate coverage of the distal ends of the plates the plate haptics can sometimes dislocate, one of the plates vaulting forwards to configure the lens in a "Z" shape configuration.

Moreover, these designs do not permit adequate movement of the optic to a change in vitreous cavity pressure to allow many patients to read comfortably at near without glasses. In order to increase the movement of the optic to respond to the increase in vitreous cavity pressure that occurs during ciliary muscle constriction, the transverse hinge connecting the haptic and the optic may be weakened by elongating the hinge or reducing its width. However, such alterations tend to destabilize the lens optic and make it prone to tilting.

SUMMARY OF THE INVENTION

An accommodating intraocular lens according to an embodiment of the present invention is described that overcomes the deficiencies of present designs noted above.

Other features and advantages of the present invention will become apparent from the following more detailed description, taken in conjunction with the accompanying drawings, which illustrate, by way of non-limiting example only, the principles of the presently described invention.

BRIEF DESCRIPTION OF THE DRAWINGS

Illustrated in the accompanying drawing(s) is at least one of the best mode embodiments of the present invention In such drawing(s).

DETAILED DESCRIPTION OF THE PREFERRED EMBODIMENT

The above described drawing figures illustrate the described invention in at least one of its preferred, best mode embodiment, which is further defined in detail in the following description. Those having ordinary skill in the art may be able to make alterations and modifications to what is described herein without departing from its spirit and scope. While this invention is susceptible of embodiment in many different forms, there is shown in the drawings and will herein be described in detail a preferred embodiment of the invention with the understanding that the present disclosure is to be considered as an exemplification of the principles of the invention and is not intended to limit the broad aspect of the invention to the embodiment illustrated. Therefore, it should be understood that what is illustrated is set forth only for the purposes of example and should not be taken as a limitation on the scope of the present apparatus and its method of use.

An IOL according to at least one preferred embodiment will now be described with reference to FIGS. 1-5.

Figure 1A:
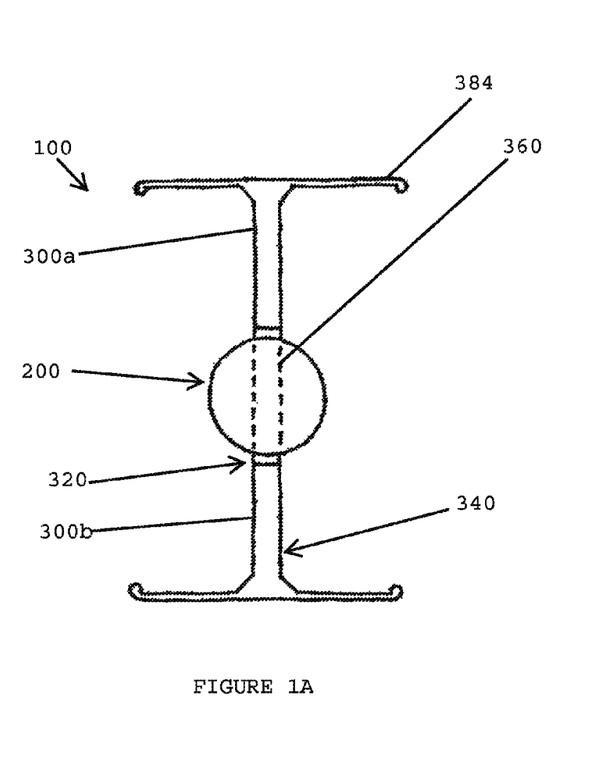
FIGS. 1A and 1B are a top plan view and a side plan view, respectively, of an IOL according to at least one embodiment of the present invention.
Figure 1B:
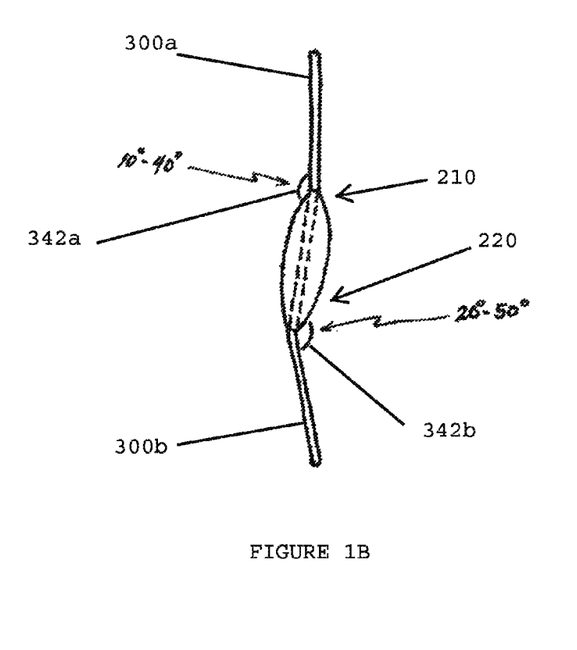

An intraocular lens (IOL) 100 comprises: an optic 200 coupled to at least one haptic 300 at a flexion 342 that sets a non-zero angle between the optic 200 and the at least one haptic 300.

The IOL 100 is placed into the capsular bag of a patient's eye after cataract surgery via known techniques such as, for example, phacoemulsification. The lens is centered so that the optical axis of the lens coincides with that of the patient's eye. The haptics 300 contact the capsular bag and the natural fibrosis of the tissue secures the haptics 300, and consequently the IOL 100, in place. Because of the non-zero angle, the IOL provides seamless near to distance vision.

The optic 200 is preferably a single focus optic that gathers the incoming light and focuses it on the retina of the patient so as to effect vision. The optic 200 may be bioconvex, refractive, diffractive, plano-convex, Fresnell, spheric, aspheric, toric, or of any other type that is substantially single focus. In order to permit the optic 200 to be inserted into the eye through a small incision, the optic 200 is preferably made of a flexible optical material, such as, for example, silicone, acrylic, hydrogel, or other flexible optical material now known or hereafter developed. Additionally, the optic may contain a UV blocker.

As shown in FIGS. 1A and 1B, the optic 200 is coupled to at least one haptic 300 having distal 320 and proximal 340 ends. Flexion 342 substantially biases the optic 200 with respect to the distal end 320 of the haptic 300, and comprises the proximal end 340 set at a non-straight angle with respect to the distal end 320.

In a preferred embodiment, the IOL comprises opposing first and second haptics 300a and 300b. Flexion 342a biases a superior hemisphere 210 of the optic 200 substantially posteriorly with respect to distal end and sets an angle between proximal and distal ends. Flexion 342b biases an inferior hemisphere 220 of the optic 200 anteriorly with respect to the distal end and sets an angle between the proximal and distal ends. Thus, as seen in FIG. 1B, the profile of the IOL 100 resembles a stretched out "Z" resulting in a tilted optic. And, as show in FIG. 3, this stretched out "Z" shape permits the anteriorly biased portion of the lens (i.e. the inferior hemisphere 220) to focus light for near vision, and the posteriorly biased portion of the lens (i.e. the superior hemisphere 210) to focus light for far vision. The lens optic will thus focus objects from distance to near seamlessly. In at least one embodiment, each flexion 342a and 342b is preferably at an angle that is not less than 10 degrees and not more than 50 degrees. Preferably, anterior flexion 342a is at an angle from approximately 10 degrees to approximately 40 degrees, while posterior flexion 342b is at an angle from approximately 20 degrees to approximately 50 degrees.

In at least one embodiment, the IOL is place within the capsular bag with the anterior flexion 342a located at a twelve o'clock position in the eye, and the posterior flexion 342b located at a six o'clock position of the eye. In this manner, the inferior hemisphere 220 of the optic lies forward of the superior hemisphere 210 and focuses light for near vision, while the superior hemisphere 210 of the optic lies rearward of the inferior hemisphere 220 and focuses light for distance vision. The aforementioned orientation mimics the orientation of external bifocals for convenience of the patient, but a reverse orientation may also be utilized.

Turning to FIG. 1A, a central element 360 may extend through the center of the optic 200 and protrude slightly on opposing sides thereof and couple the optic 200 to opposing haptics 300a and 300b. In some embodiments, the central element 360 and opposing haptics 300 may comprise one contiguous structure, the central element 360 of which passes through the center of the optic 200. In a preferred embodiment, the central element 360 comprises a flat rigid piece over which is molded the flexible optic 200. In order to maintain optical integrity, it is preferable that the central element 360 have a refractive index that is the same or substantially similar to the optic 200. Preferably, the central element is made of the same or similar, flexible, semi-rigid or substantially non-flexible material, as the haptics 300, including but not limited to: acrylic, PMMA, polycarbonate, nylon, or similar clear optical material.

Turning now to FIG. 1B, the at least one haptic 300 is preferably a substantially rigid plate haptic 300 having distal 320 and proximal 340 ends angularly set so as to form flexion 342. The rigid plate haptic 300 operates to engage, fixate and center the haptic into the capsular bag. The haptic may be such as to enable insertion into the eye via a small incision. In at least one embodiment, the plate haptic is between 2.0 mm to 5.0 mm wide and between 9.0 mm to 11.0 mm long. It is preferable that the haptic body be constructed of the same or similar flexible or semi-rigid material as the optic, including, but not limited to: silicone, hydrogel, acrylic, or similar material.

Flexible projections 384, or fingers, may extend from the distal end 320 to engage the capsular bag and secure and center the IOL 100 thereto. The projections 384 may be homogeneous and may be made of either polyimide, PMMA, acrylic or any other inert material.

Figure 4A:
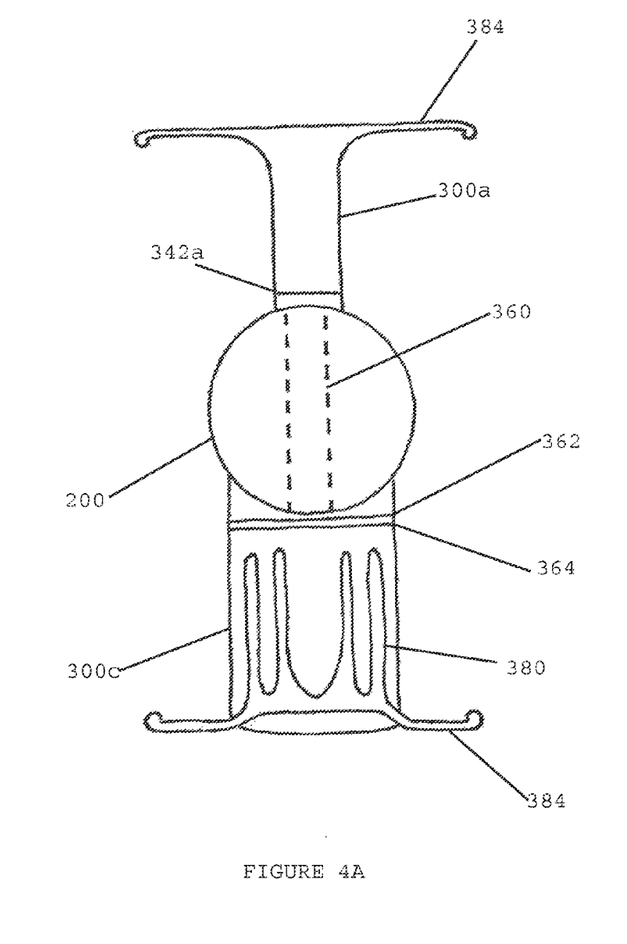
FIGS. 4A and 4B are a top plan view and a side plan view, respectively, of an IOL according to at least one embodiment of the present invention.
Figure 4B:
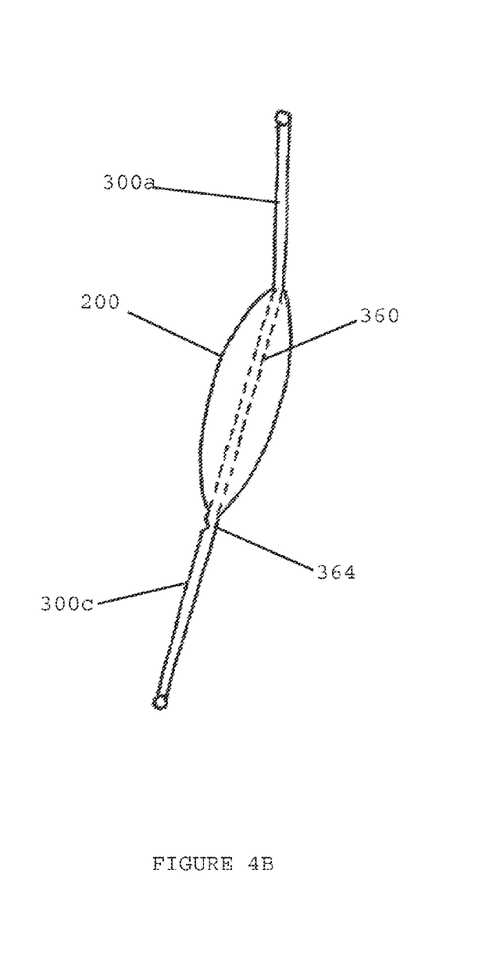
Figure 5A:
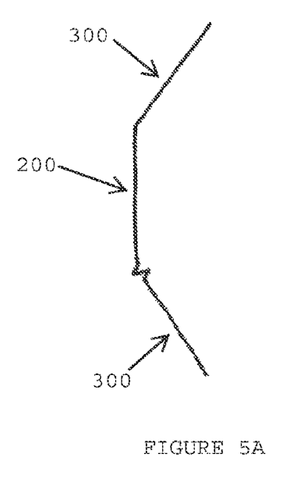
FIGS. 5A-5F consists of a progression of side plan views of an IOL according to at least one embodiment of the present invention.
Figure 5B:
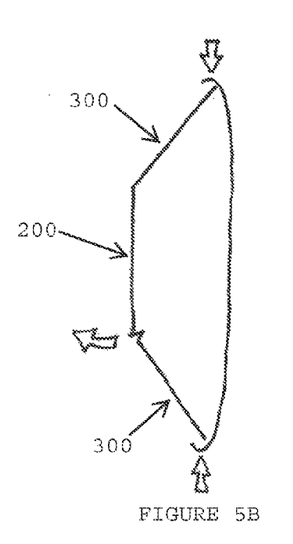
Figure 5C:
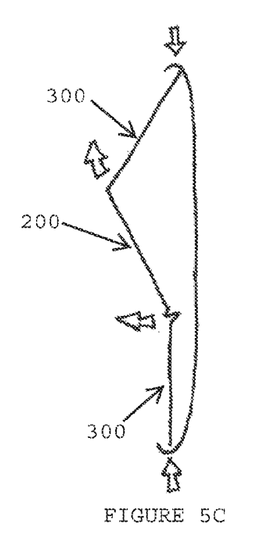
Figure 5D:
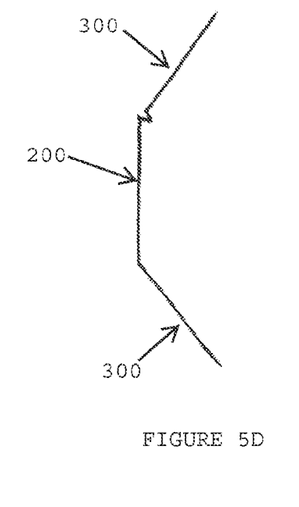
Figure 5E:
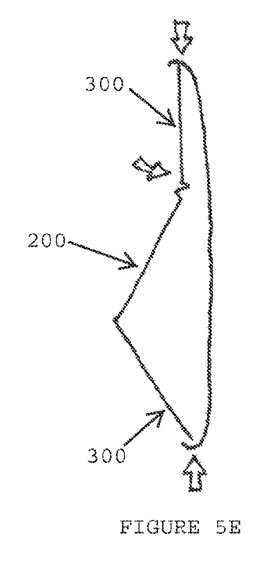
Figure 5F:
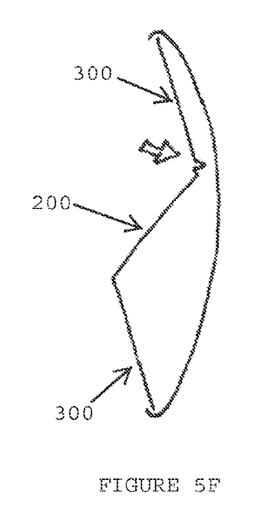

Turning to FIGS. 4A and 4B, in at least one embodiment, the optic 200 is coupled to a substantially rigid plate haptic 300a and a semi-flexible plate haptic 300c. Plate haptic 300a has distal 320 and proximal 340 ends angularly set so as to form flexion 342, as discussed herein, and is coupled to central element 360 extending through the optic 200. Plate haptic 300c is operable to permit accommodation of the associated portion of the IOL and is be coupled to the optic 200 via a flexible connecting member 362 made of the same or similar flexible material as the optic 200.

The connecting member 362 may comprise a hinge 364 extending transversely across either or both sides that is an area of the connecting member 362 that operates to weaken the connecting member 362 so that vitreous pressure can stretch the base of the hinge 364 like an elastic band to allow the optic 200 to move forward. In this manner, the IOL is able to partially accommodate according to the semi-flexible plate haptic 300c and is also able to provide seamless distance to near vision.

The semi-flexible plate haptic 300c operates to engage, fixate and center the haptic into the capsular bag so as to move centrally and posteriorly in response to ciliary muscle flexion, as shown in FIGS. 5A-5F, such movement, combined with the change in vitreous pressure and end-to-end compression of the distal ends 340 of the haptics 300 via contraction of the ciliary muscles, causing the associated hemisphere of the optic 200 to move forward.

The haptic 300c may be substantially flexible in the transverse direction and substantially rigid in the longitudinal direction so as to enable folded insertion into the eye via a small incision. A frame 380 may be embedded within the haptic body so as to promote the longitudinal rigidity thereof. The frame 380 may be formed of polyimide, prolene, polymethylmethanylate (PMMA), titanium, or similar material. One of ordinary skill will appreciate that while substantial rigidity may promote vaulting; the degree of rigidity imposed is not intended to preclude an effective vault of the optic at the connecting member 362. It is preferable that the haptic be constructed of the same or similar flexible or semi-rigid material as the optic, including, but not limited to: silicone, hydrogel, acrylic, or similar material.

As shown in FIG. 4A, the frame 380 may be integral with projections 384, or fingers, that extend from the distal end 320 to engage the capsular bag and secure and center the IOL 100 thereto. The projections 384 may be homogeneous and may be made of either polyimide, PMMA, acrylic or any other inert material.

Exemplary semi-flexible plate haptics are described in U.S. Ser. Nos. 13/017,189; 13/092,359; 13/111,599; and 13/155,327, incorporated herein by reference in their entireties.

In at least one embodiment, the longitudinal length of the IOL (i.e. from distal end to distal end) may be between approximately 9.0-11.0 mm, with the diameter as measured from the tips of the lateral projections being between approximately 11.5-12.0 mm. The haptics 300 are preferably between 2.0-6.0 mm wide and 0.20-0.75 mm thick, while the optic may be approximately 4.5-6.0 mm in diameter.

An IOL according to at least one preferred embodiment will now be described with reference to FIGS. 6-9.

Figure 6:
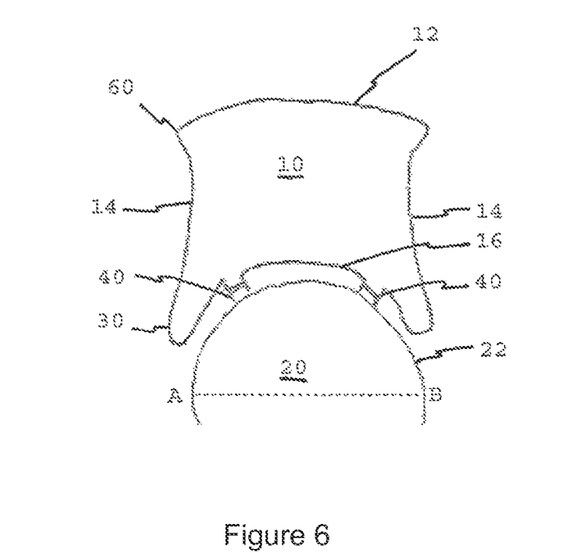
FIG. 6 is a top view of an exemplary plate haptic coupled to an optic according to at least one embodiment of the present invention.

As illustrated in FIG. 6, an intraocular accommodating lens may comprise at least one plate haptic 10 and a lens optic 20.

The plate haptic 10 may comprise a distal portion 12, opposing lateral portions 14, and a proximal portion 16. In at least one preferred embodiment, the plate haptic 10 may be substantially or partially constructed of flexible material, such as silicone, acrylic, hydrogel, and/or similar materials known in the art.

The plate haptic 10 may be of solid, unitary construction, and may have tapered, rounded or parallel edges. In some embodiments, the plate haptic 10 may be between 5.0 and 6.0 mm in width, and between 0.2 to 0.75 mm in thickness. Preferably, the longitudinal length or circumference diameter of the plate haptic 10 may be between 10.0 to 12.0 mm.

Figure 2:
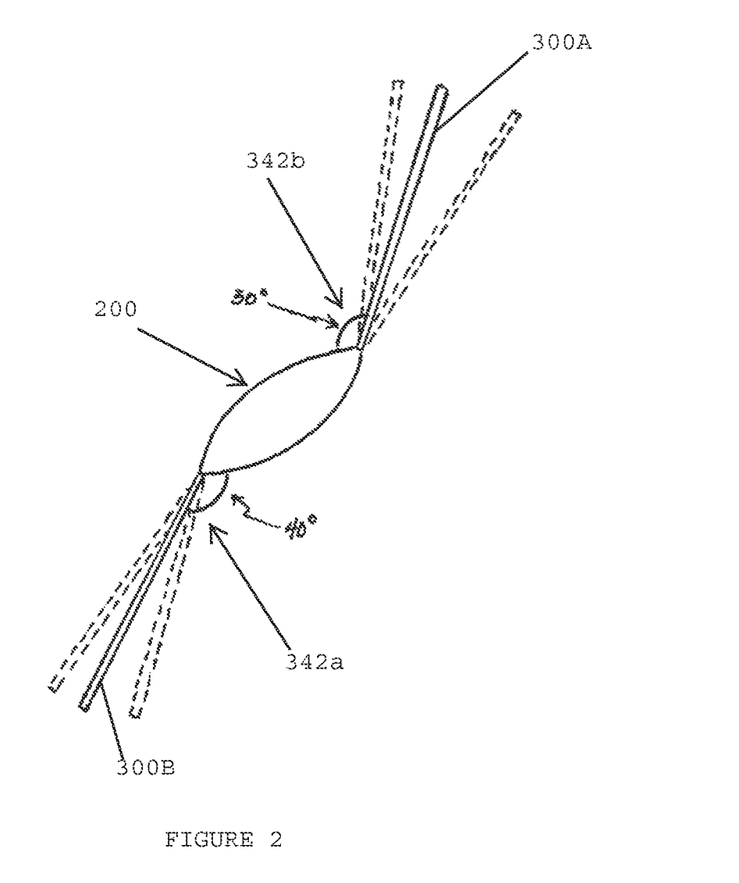
FIG. 2 is a side plan view of an IOL having flexions according to at least one embodiment of the present invention.
Figure 3:
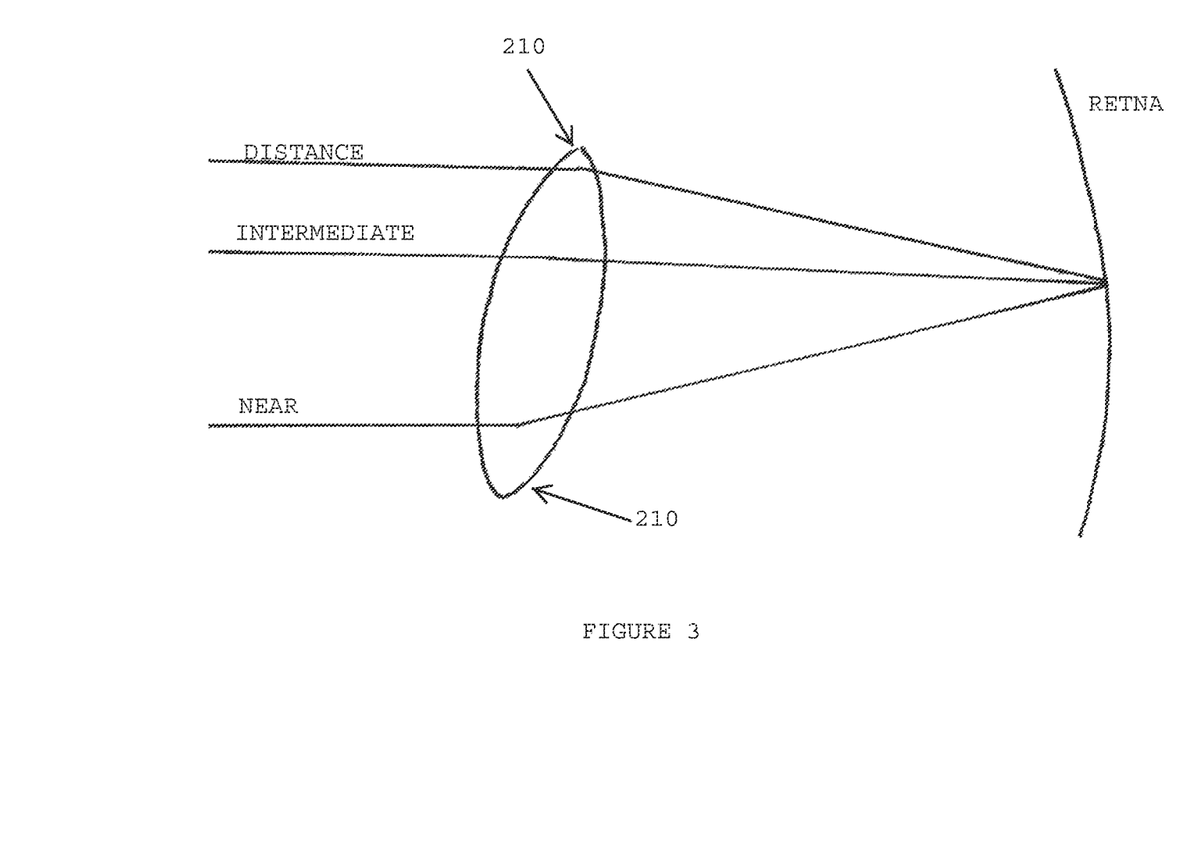
FIG. 3 is a schematic view of an IOL tilted according to at least one embodiment of the present invention.

The lens optic 20 may comprise a periphery 22 and a transverse diameter defined by points A and B, as shown in FIGS. 2 and 3. In at least one preferred embodiment, the proximal portion 16 is substantially parallel to the periphery 22 and contoured thereto. In at least one preferred embodiment, the lens optic 20 comprises at least one of: solid, single, multifocal, Fresnell, toric, biconvex, piano-convex refractive, diffractive or liquid filled optics. In at least one preferred embodiment, the lens optic 20 may be substantially or partially constructed of flexible material, such as silicone, acrylic, hydrogel, and/or similar materials known in the art.

Figure 7:
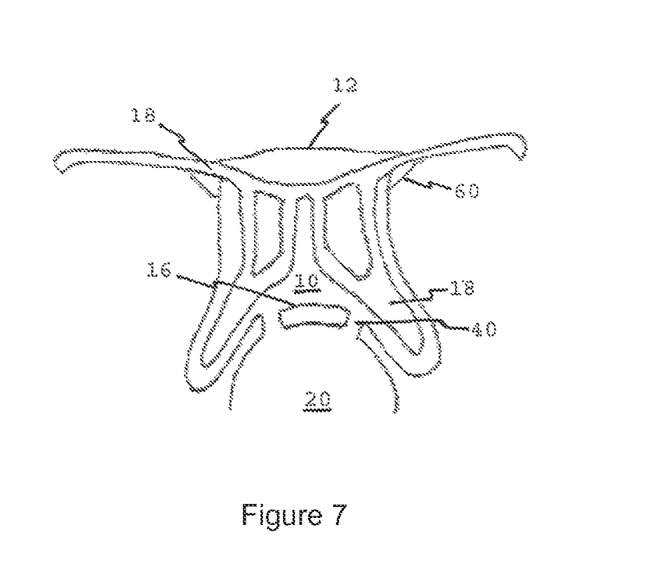
FIG. 7 is a top view of an exemplary plate haptic coupled to an optic according to at least one embodiment of the present invention.

As illustrated in FIG. 7, in at least one preferred embodiment, the plate haptic 10 may comprise a chassis 18. The chassis 18 may be operable to permit flexion of the plate haptic 10 in the longitudinal direction and to substantially resist and prevent flexion of the plate haptic 10 in the transverse direction. This discriminatory flexion permits the lens to be inserted into an eye in a compact state while resisting bending in response to vitreous pressure from the eye once it is inserted.

In at least one preferred embodiment, the chassis 18 may be a semi-rigid chassis 18 constructed of at least one of: silicone, acrylic, hydrogel, polyamide, prolene, PMMA and titanium. It should be observed that according to at least one preferred embodiment, the chassis 18 may be constructed of the same material as either or both of the plate haptic 10 and the lens optic 20. In some embodiments, the chassis 18 may consist of portions of increased thickness of the plate haptic 10. In shape, the chassis 18 preferably comprises an irregular web throughout the plate haptic 10, however, regular and repeated frame elements are specifically contemplated.

In at least one preferred embodiment, the proximal portion 16 of the plate haptic 10 comprises a flexible junction 40 connecting the lens optic 20 to the plate haptic 10, as shown in FIGS. 6-7. The flexible junction 40 may be operable to reduce the resistance of the lens optic 20 to a change in vitreous cavity pressure, thereby allowing more movement of the lens optic 20 along the axis of the eye.

The flexible junction 40 may comprise a single strap, or may comprise a plurality of spaced apart flexible straps. The strap or straps may extend substantially longitudinally from the proximal portion 16 of the plate haptic 10 and connect the plate haptic 10 to the periphery 22 of the lens optic 20. Alternatively, the strap or straps may extend substantially radially from the periphery 22 of the lens optic 20 and connect the lens optic 20 to the proximal portion 16 of the plate haptic 10. As illustrated in FIG. 6, each strap may have one or more hinges 50 laterally traversing the strap and weakening the strap 40 so as to promote stretching and flexion thereat. The hinge may consist of a single groove. Alternatively, the hinge may consist of two or more directly or indirectly opposing grooves.

Returning to FIG. 6, in at least one preferred embodiment, each lateral portion 14 along with the proximal portion 16 forms an appendage 30. Thus, the plate haptic 10 may comprise a plurality of appendages 30, and preferably comprises two appendages 30 that together partially surround the lens optic 20. The appendage may be paddle shaped but is not limited thereto and should be understood through its functionality. As the ciliary muscle contracts it exerts an inwardly radial end-to-end pressure on opposing plate haptics 10 which are then forced centrally and posteriorly. Because the appendages 30 partially surround the optic 20, increased pressure is exerted by the vitreous cavity, thereby increasing displacement of the lens optic 20 along the axis of the eye.

Figure 9:
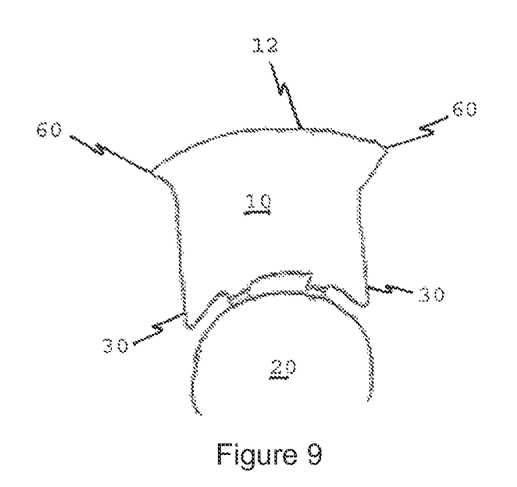
FIG. 9 is a top view of an exemplary plate haptic coupled to an optic according to at least one embodiment of the present invention.

In some embodiments, the appendages 30 may extend from the proximal portion 16 at an angle that is substantially between complete lateral extension and complete longitudinal extension. Alternatively, as shown in FIG. 9, the appendages 30 may extend from the proximal portion 16 at an angle that is substantially longitudinal. In at least one preferred embodiment, the appendages 30 are positioned substantially more laterally than the straps.

Figure 8:
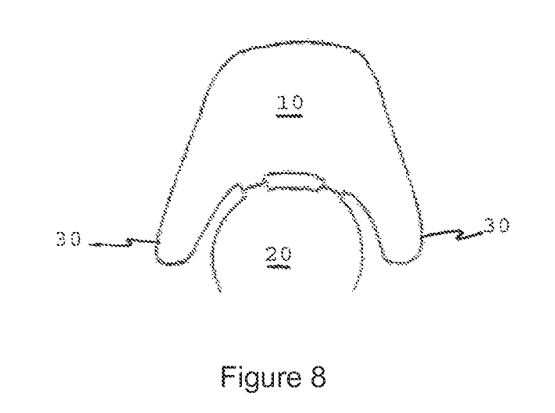
FIG. 8 is a top view of an exemplary plate haptic coupled to an optic according to at least one embodiment of the present invention.

Turning now to FIG. 8, in some embodiments, the lateral extension of the appendages 30 may be greater than the transverse diameter of the lens optic 20. In other words, the appendage may extend out beyond an imaginary line tangent to the lateral most point(s) of the lens optic 20 periphery 22. In some embodiments, the lateral extension of the appendages 30 may be such that the lateral portions 14 are substantially co-extensive with the transverse diameter of the lens optic 20, as shown in FIG. 9.

As discussed above, each appendage 30 is formed of the lateral portion 14 and proximal portion 16. In some embodiments, the lateral portions 14 of opposing appendages 30 may be substantially non-convergent. In other words, the lateral portion 14 may be approximated by lines which, if extended roughly in the direction of the lens optic 20, would be substantially non-convergent. In at least one preferred embodiment, the lateral portion 14 may be substantially divergent, as shown in FIG. 8. In at least one preferred embodiment, they may be substantially parallel, as shown in FIG. 9.

The appendages 30 may be of any shape that substantially extends the contact area of the plate haptic 10 with the capsular bag thereby increasing vitreous pressure response. As illustrated in FIG. 4, in at least one preferred embodiments, the appendage 30 may be partially triangular in shape—the lateral portion 14 and proximal portion 16 comprising two sides of a triangle. As illustrated in FIGS. 6-8, in at least one other preferred embodiment the appendage 30 may be curved and may be partially elliptical in shape. For example, the appendage may be substantially paddle, or tear-drop shaped—the lateral portion 14 and proximal portion 16 approximating the curve. In some embodiments, the appendage 30 may be between 2.0 to 7.0 mm in width. In some embodiments, the appendage 30 may be between 0.02 to 0.75 mm in thickness.

The appendages 30 may be of fully or partially rigid construction. In some embodiments, the appendages 30 are partially or wholly constructed of flexible material such as: silicone, acrylic, hydrogel, and the like. In some embodiments the appendages 30 are partially or wholly constructed of substantially rigid or semi-rigid material such as: polyamide, prolene, PMMA, titanium and the like. In some embodiments, the appendages 30 at least partially include at least a portion of the chassis 18, as shown in FIG. 7.

Turning now to FIGS. 6-9, in at least one preferred embodiment, the distal end is convex so as to increase a contact surface area. Furthermore, in at least one preferred embodiment, each lateral portion 14 along with the distal portion 12 forms a projection 60, as shown in FIGS. 6-7 and 9. Thus, the plate haptic 10 may comprise a plurality of projections 60, and preferably comprises two projections 60 that may extend substantially laterally from the distal portion 12. The projections 60 may further increase the area of contact between the distal portion 12 of the plate haptic 10 and the capsular bag of the eye. Preferably, the projections 60, in combination with the distal portion 12 may substantially occupy the cul de sac of the capsular bag. In at least one embodiment, the projections 60 may be partially triangular, elliptical, curved, or of any shape operable to increase the contact area. The projections 60 may also comprise a portion of the chassis 18, as shown in FIG. 7.

In at least one embodiment, the intraocular accommodating lens comprises a plurality, and preferably a pair, of opposing plate haptics 10, each connected to the lens at respective flexible junctions 40. In some embodiments, however, the intraocular accommodating lens comprises a single plate haptic 10 opposing a non-plate haptic 10 of a type known in the art.

An IOL according to at least one preferred embodiment will now be described with reference to FIGS. 10-17.

Figure 10:
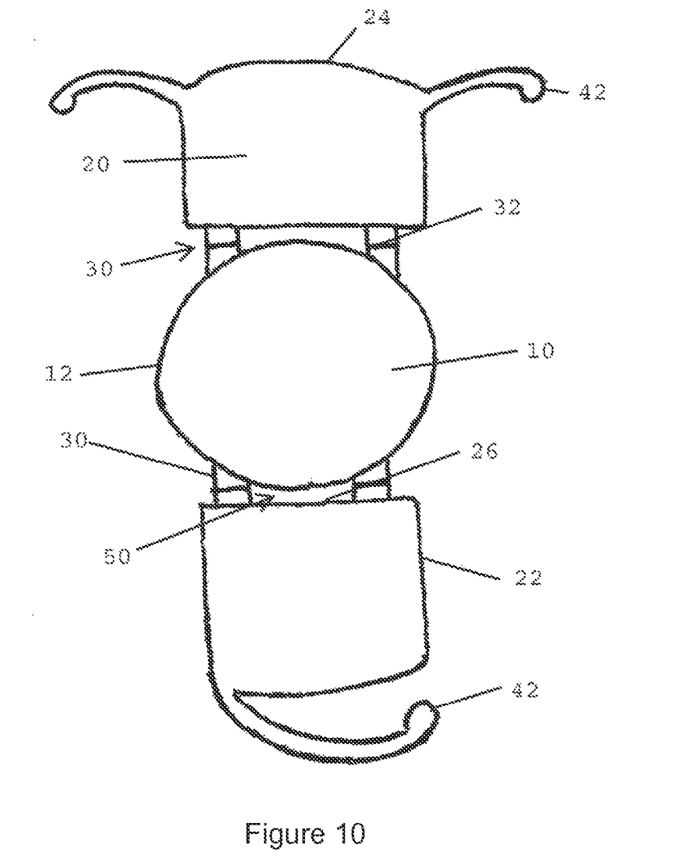
FIG. 10 is a top view of an IOL according to at least one embodiment of the present invention.

FIG. 10 illustrates a tilt stabilizing AIOL according to a preferred embodiment. A lens optic 10 is flexibly coupled to a plurality of opposing plate haptics 20 via a plurality of spaced apart coupling members 30. The tilt stabilizing AIOL is operable to be inserted into an eye having a ciliary body, and is responsive to vitreous pressure changes in the eye such that an increase in vitreous pressure caused by contraction of the ciliary muscle about the plate haptics 20 causes the lens optic 10 to be displaced in a substantially anterior direction A so as to accommodate near vision, and a decrease in vitreous pressure caused by 30 relaxation of the ciliary muscle about the plate haptics 20 causes the lens optic 10 to be displaced III a substantially posterior direction P for distance vision, as shown in FIGS. 2b and 2a.

Returning to FIG. 10, at least one pair of diametrically opposed plate haptics 20 are longitudinally coupled to the lens optic 10 periphery 12 via the coupling members 30. In at least one embodiment, the lens optic 10 is stabilized by plate haptics 20 having a width equal to or greater than the diameter of the lens optic 10. In some embodiments, the width of the plate haptic 20 is between 4.0 and 6.0 mm, and the thickness of the plate haptic is between 0.15 and 0.4 mm.

Figures 13, 14:
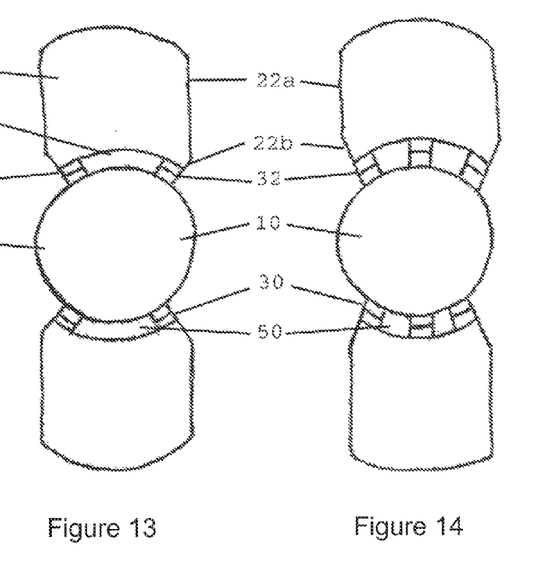
FIG. 13 is a top view of an IOL according to at least one embodiment of the present invention.
FIG. 14 is a top view of an IOL according to at least one embodiment of the present invention.

In some embodiments, the lens optic 10 is further stabilized by plate haptics 20 having parallel sides 22. In other embodiments, the lens optic 10 may be stabilized by plate haptics 20 having sides which have parallel portions 22a and non-parallel portions 22b. In at least one embodiment, the non-parallel portions 22b may be substantially convergent, as shown in FIGS. 13-14, but divergent non-parallel portions are specifically contemplated. The plate haptic is preferably made of substantially of silicone, hydrogel, acrylic, or similar material.

A plurality of spaced apart connecting members 30 flexibly couple the lens optic 10 to each plate haptic 20, forming at least one aperture 50 defined by the lens optic 10, the plate haptic 20 and the spaced apart coupling members 30. In order to aid in lens optic 10 stabilization, in at least one embodiment, the connecting members 30 extend radially from the lens optic 10 to the haptic 20. However, other embodiments stabilize the lens optic 10 with connecting members 30 that extend longitudinally from the plate haptic 20 to the lens optic 10. The connecting members are preferably narrow, thin straps, but may be any structure permitting longitudinal stretching and flexion. In at least one embodiment, the connecting member is between 0.5 to 2.0 mm in width.

As illustrated in FIG. 10, two or more straps 30 are preferably used to couple each 30 haptic 20 to the lens optic 10. The straps 30 are preferably equidistant from a longitudinal axis of the AIOL and the space between them defines the aperture 50 along with the lens optic 10 and the plate haptic 20. While preferred embodiments illustrate multiple straps 30, at least one embodiment is contemplated that comprises a single strap 30 that may be of varying thickness.

Figure 12:
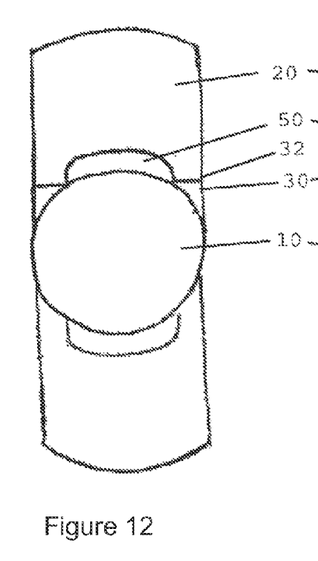
FIG. 12 is a top view of an IOL according to at least one embodiment of the present invention.

FIG. 12 illustrates an embodiment wherein at least two straps 30 couple each haptic 20 to the lens optic 10. Straps 30 extend longitudinally from each haptic 20 to the lens optic 10 so as to couple each haptic 20 to the lens optic 10. As shown in FIG. 3, the connecting members 30 may be wholly or partially formed as right triangles of flexible 10 material with their hypotenuses fixed to the lens periphery 12. The groove 32 may also be substantially adjacent the proximal end 26 of the haptic, as shown.

FIG. 13 illustrates an embodiment wherein connecting members 30 extend substantially radially from the optic periphery 12 to couple the optic 10 to a curved proximal end 26 of the haptic 20 that is substantially parallel to the optic periphery 12. Additionally, the haptic is shown to have substantially converging non-parallel sides 22b adjacent the proximal end 26. While the proximal end 26 is shown as curving so as to run parallel with the optic periphery 12, the proximal end 26 may also be substantially straight so as to run tangential to the optic periphery 12 and/or the proximal end 26.

FIG. 14 illustrates an embodiment wherein at least three connecting members 30 extend radially from the lens optic periphery 12 to the haptic proximal end 26. The connecting members 30 comprise at least one opposing pair of outer connecting members 30a and a central connecting member 30b. The outer connecting members 30a making up an opposing pair are preferably equidistant from the longitudinal axis of the AIOL, and extend radially from the optic periphery 12 to the proximal end 26 of the haptic. The outer connecting members may comprise a plurality of opposing pairs of connecting members 30a, or a single opposing pair of connecting members 30a. The central connecting member 30b is aligned with the longitudinal axis of the AIOL and extends radially from the optic periphery to the proximal end of the haptic.

Figure 15:
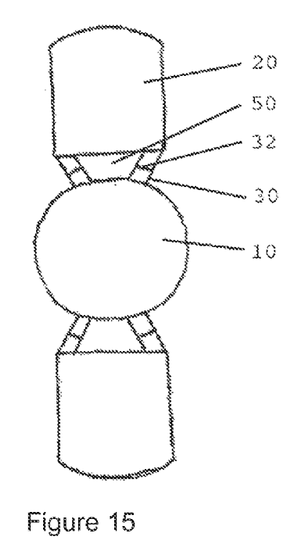
FIG. 15 is a top view of an IOL according to at least one embodiment of the present invention.
Figure 16:
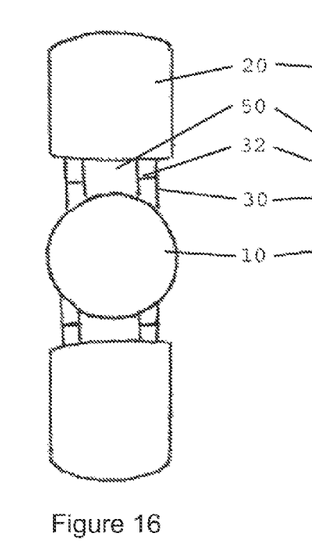
FIG. 16 is a top view of an IOL according to at least one embodiment of the present invention.
Figure 17:
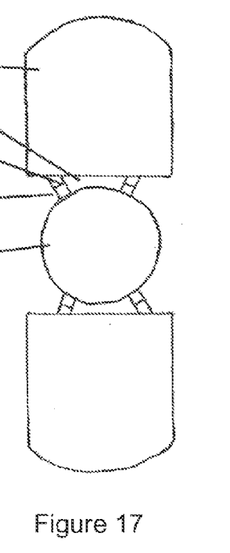
FIG. 17 is a top view of an IOL according to at least one embodiment of the present invention.

FIGS. 15-17 illustrate connecting member 30 placement according to various embodiments. FIG. 15 shows connecting members 30 extending radially from parallel sides 22 of the plate haptic 20 whose width is less than the diameter of the lens optic 10. FIG. 16 shows connecting members 30 extending radially from parallel sides 22 of the plate haptic whose width is greater than the diameter of the lens optic 10. FIG. 17 shows connecting members 30 extending longitudinally from the plate haptic 20 to the lens optic 10, the plate haptic 20 being substantially the same width as the lens optic 10, the connecting members 30 being substantially parallel.

Turning now to FIG. 10, each connecting member 30 preferably comprises a first surface 32 and a second surface 34 opposed thereto. The first surface 32 may comprise a groove, channel or hinge 36 that weakens the connecting member 30 and increases stretching, elongation and flexion at the hinge 36. The groove 36 preferably traverses the connecting member 30 in at least one of: a lateral direction, parallel to the optic periphery, tangential to the optic periphery, parallel to the haptic proximal end, and tangential to the haptic proximal end, but may also traverse the connecting member through non-parallel, non-lateral, or non-linear paths. Thus, the groove 36 may be straight, curved or any combination thereof. In at least some embodiments, the second surface may also comprise a groove, channel or hinge 36 to further weaken the connecting member 30. The hinge 36 may have a thickness that is half the thickness of the plate haptic, or preferably a thickness of 0.10 to 0.30 mm. In at least one embodiment, multiple grooves 36 are present on at least one of the first 32 and second 34 surface.

Returning now to FIG. 10, preferably, each plate haptic 20 comprises a distal end 24 having a centration fixation component 42. The centration fixation component 42 is preferably T-shaped, and comprises a pair of curved loops 42 extending in an arc from either lateral side of the distal end 24 of the haptic 20. In at least one embodiment, the loop 42 curves substantially towards the lens optic 10. However, in at least one other embodiment, the centration fixation component 42 comprises a single curved loop extending in an arc from one lateral side of the distal end 24 of the haptic to the other lateral side of the distal end 24 of the haptic. It is important to note that each plate haptic may comprise a different centration fixation component, for example, as show in FIG. 1, or none at all. In one embodiment, the length of the tilt stabilizing AIOL without the centration fixation component 42 is 10.5 to 11.0 mm, while the length of the tilt stabilizing AIOL with the centration fixation component 42 is 11.5 to 12.5 mm. The flexible loops 42 are preferably compressible centrally to fix and center the AIOL within the capsular while minimizing tilt.

The centration fixation component 42 may be of the same material as the plate haptic 20 and/or the lens optic 10, or may be polyimide, prolene, polymethylmethanylate (PMMA), titanium or similar material. In one embodiment, the projection comprises a homogenous integral part of the plate haptic. In another embodiment, the projection comprises a distinct unit set into the plate haptic during molding. Preferably, the projections measure from 2.0 to 4.0 mm in length extending from the distal end of the haptic and are flexible extending to a transverse diameter that exceeds the diameter of the capsular bag.

The lens optic 10 is preferably a solid refractive single vision optic, however other optics are contemplated. For example, the lens optic 10 may be at least one of: solid, single vision, multifocal, Fresnell, spheric, aspheric, toric, biconvex, piano-convex, liquid filled, diffractive or refractive. Additionally, the lens optic 10 is preferably constructed of a flexible optical material such as silicone, hydrogel or acrylic material, but may be made of any similar material. In at least one embodiment, the lens optic has a diameter of 5.0 mm.

According to one embodiment, when the AIOL is implanted into the capsular bag of the eye, the plate haptics 20 and its loops 42 contact the periphery of the capsular bag and operate to support the optic 10 within the eye and to substantially align and fix the lens into 30 the capsular bag, thereby centering the lens optic 10 along the optical axis of the eye. The flexible projections 42 extend beyond the diameter of the capsular bag. Lateral and distal end extensions (not shown) may be provided to contact the periphery of the capsular bag, thereby increasing the contact area of the lens within the bag and providing additional fixation and support to for the lens within the capsular bag.

Figure 11A:
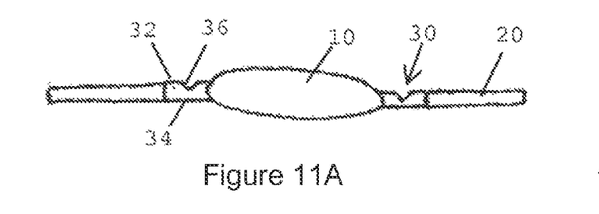
FIGS. 11A and 11B illustrate side views of an IOL during accommodation according to at least one embodiment of the present invention.
Figure 11B:
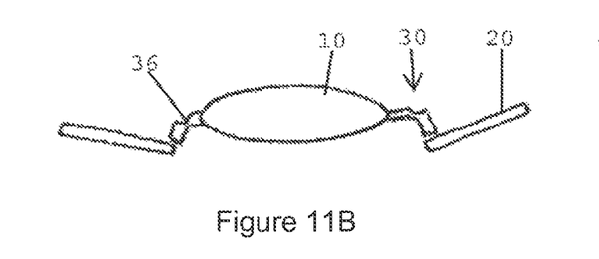

As illustrated in FIGS. 11A and 11B, during accommodation the ciliary muscle exerts radial pressure on the ends of the haptics 20. The plate haptics 20, which naturally vault backwards when placed into the capsular bag, are thus moved centrally and posteriorly, towards the optic 10. The haptic 20 resists bending to the radial force exerted by the ciliary 10 muscle. However, the stretchable thin hinge 32 across the flexible connecting members 30 is less resistant to the pressure from the vitreous cavity, and therefore stretches and flexes on application of the pressure. The separation of multiple connecting members 30 ensures the transferred pressure is uniform. With this increase in vitreous cavity pressure, the optic 10 is thus pushed forward along the axis of the eye by the stretching of the thin base of the hinge 32, the optic 10 moving forward relative to both the proximal 26 and distal ends 24 of the plate haptics 20, resulting in accommodation.

The enablements described in detail above are considered novel over the prior art of record and are considered critical to the operation of at least one aspect of the invention and to the achievement of the above described objectives. The words used in this specification to describe the instant embodiments are to be understood not only in the sense of their commonly defined meanings, but to include by special definition in this specification: structure, material or acts beyond the scope of the commonly defined meanings. Thus if an element can be understood in the context of this specification as including more than one meaning, then its use must be understood as being generic to all possible meanings supported by the specification and by the word or words describing the element.

The definitions of the words or drawing elements described herein are meant to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for anyone of the elements described and its various embodiments or that a single element may be substituted for two or more elements in a claim.

Changes from the claimed subject matter as viewed by a person with ordinary skill in the art, now known or later devised, are expressly contemplated as being equivalents within the scope intended and its various embodiments. Therefore, obvious substitutions now or later known to one with ordinary skill in the art are defined to be within the scope of the defined elements. This disclosure is thus meant to be understood to include what is specifically illustrated and described above, what is conceptually equivalent, what can be obviously substituted, and also what incorporates the essential ideas.

The scope of this description is to be interpreted only in conjunction with the appended claims and it is made clear, here, that the named inventor believes that the claimed subject matter is what is intended to be patented.

What is claimed is:

1. A seamless focus intraocular lens (IOL) comprising:
a first rigid plate haptic and an opposite second rigid plate haptic, each of said opposing first and second haptics having a distal end and a proximal end,
a biconvex optic comprising a superior hemisphere and an inferior hemisphere;
wherein the first rigid plate haptic is coupled to the optic at a first flexion, wherein the first flexion biases the superior hemisphere of the optic substantially posteriorly and sets a fixed first non-zero angle between the optic and the first plate haptic,
wherein the second rigid plate haptic is coupled to the optic at a second flexion, wherein the second flexion biases the inferior hemisphere of the optic substantially anteriorly and sets a fixed second non-zero angle between the optic and the second rigid plate haptic, the second non-zero angle being different from the first non-zero angle,
wherein the superior hemisphere is adapted to be positioned at the twelve o'clock position in the eye and configured to focus light for distant vision, and the inferior hemisphere is adapted to be positioned at the six o'clock position in the eye and configured to focus light for near vision,
wherein the profile of the IOL resembles a stretched out "Z" resulting in a tilted optic, and
wherein the intraocular lens provides seamless distance to near vision.

2. A seamless focus intraocular lens according to claim 1, wherein a material from which the optic is made is semi-rigid.

3. A seamless focus intraocular lens according to claim 2, wherein the material comprises acrylic, silicone, or hydrogel.

4. A seamless focus intraocular lens according to claim 1, wherein the first non-zero angle is not less than 10 degrees and not more than 50 degrees.

5. A seamless focus intraocular lens according to claim 1, wherein the first rigid plate haptic comprises one or more lateral extensions extending from the distal end of the first rigid plate haptic.

6. A seamless focus intraocular lens according to claim 1, wherein the first rigid plate haptic is coupled to the superior hemisphere of the optic when the lens is placed into a capsular bag of an eye.

7. A seamless focus intraocular lens according to claim 4, wherein the second non-zero angle is at least about 20 degrees and less than or equal to about 50 degrees.

* * * * *